(12) United States Patent
Zhong et al.

(10) Patent No.: US 7,792,568 B2
(45) Date of Patent: Sep. 7, 2010

(54) MRI-VISIBLE MEDICAL DEVICES

(75) Inventors: Sheng-Ping Zhong, Shrewsbury, MA (US); Ronald A. Sahatjian, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1220 days.

(21) Appl. No.: 10/390,202

(22) Filed: Mar. 17, 2003

(65) Prior Publication Data

US 2004/0186377 A1    Sep. 23, 2004

(51) Int. Cl.
*A61B 5/05*    (2006.01)
(52) U.S. Cl. ............... 600/431; 600/410; 600/411; 600/420; 600/421; 600/424; 600/433; 600/435; 264/4; 264/4.1; 264/150
(58) Field of Classification Search ......... 600/410–411, 600/420, 424, 431, 433, 435, 421; 264/4, 264/4.1, 150
See application file for complete search history.

(56) References Cited

U.S. PATENT DOCUMENTS

| | | | |
|---|---|---|---|
| 4,989,608 A * | 2/1991 | Ratner ................... | 600/420 |
| 5,195,969 A | 3/1993 | Wang et al. | |
| 5,211,166 A * | 5/1993 | Sepponen ............... | 600/420 |
| 5,270,086 A | 12/1993 | Hamlin | |
| 5,366,504 A | 11/1994 | Andersen et al. | |
| 5,427,099 A | 6/1995 | Adams | |
| 5,445,151 A | 8/1995 | Darrow et al. | |
| 5,449,508 A * | 9/1995 | Unger ................... | 424/9.323 |
| 5,451,209 A | 9/1995 | Ainsworth et al. | |
| 5,674,242 A | 10/1997 | Phan et al. | |
| 5,679,470 A | 10/1997 | Mayer | |
| 5,725,570 A | 3/1998 | Heath | |
| 5,746,208 A | 5/1998 | Prince | |
| 5,782,764 A * | 7/1998 | Werne ................... | 600/411 |
| 5,868,674 A | 2/1999 | Glowinski et al. | |
| 5,895,401 A * | 4/1999 | Daum et al. ........... | 606/167 |
| 5,906,579 A | 5/1999 | Vander Salm et al. | |
| 5,908,410 A * | 6/1999 | Weber et al. ........... | 604/523 |
| 5,961,455 A | 10/1999 | Daum et al. | |
| 5,964,705 A | 10/1999 | Truwit et al. | |
| 6,026,316 A | 2/2000 | Kucharczyk et al. | |
| 6,033,645 A | 3/2000 | Unger et al. | |
| 6,061,587 A | 5/2000 | Kucharczyk et al. | |
| 6,123,920 A | 9/2000 | Gunther et al. | |
| 6,174,330 B1 * | 1/2001 | Stinson ................. | 623/1.34 |

(Continued)

FOREIGN PATENT DOCUMENTS

EP        0 775 500 A1    5/1997

(Continued)

OTHER PUBLICATIONS

International Search Report, mailed Sep. 17, 2004.

(Continued)

*Primary Examiner*—Brian Casler
*Assistant Examiner*—James Kish
(74) *Attorney, Agent, or Firm*—Crompton, Seager & Tufte, LLC (57) ABSTRACT

A medical device includes a body, a member in the body, and a contrast agent in the member. The device can be visible by magnetic resonance imaging.

37 Claims, 5 Drawing Sheets

U.S. PATENT DOCUMENTS

| | | | |
|---|---|---|---|
| 6,219,572 B1 | 4/2001 | Young | |
| 6,272,370 B1 | 8/2001 | Gillies et al. | |
| 6,278,057 B1 | 8/2001 | Avellanet | |
| 6,280,385 B1 | 8/2001 | Melzer et al. | |
| 6,315,757 B1 * | 11/2001 | Chee et al. | 604/103.09 |
| 6,322,534 B1 | 11/2001 | Shkolnik | |
| 6,324,833 B1 | 12/2001 | Singer et al. | |
| 6,342,598 B1 * | 1/2002 | Anelli et al. | 540/474 |
| 6,423,296 B1 | 7/2002 | Gunther et al. | |
| 6,428,571 B1 | 8/2002 | Lentz et al. | |
| 6,436,056 B1 | 8/2002 | Wang et al. | |
| 6,487,437 B1 | 11/2002 | Viswanathan et al. | |
| 6,512,941 B1 | 1/2003 | Weiss et al. | |
| 6,532,380 B1 | 3/2003 | Close et al. | |
| 6,574,497 B1 * | 6/2003 | Pacetti | 600/420 |
| 6,626,902 B1 * | 9/2003 | Kucharczyk et al. | 606/41 |
| 6,628,980 B2 | 9/2003 | Atalar et al. | |
| 6,638,301 B1 * | 10/2003 | Chandrasekaran et al. | 623/1.34 |
| 6,658,280 B1 * | 12/2003 | Haacke | 600/410 |
| 6,733,523 B2 * | 5/2004 | Shaolian et al. | 623/1.35 |
| 2002/0016564 A1 * | 2/2002 | Courtney et al. | 604/96.01 |
| 2002/0188195 A1 * | 12/2002 | Mills | 600/431 |
| 2004/0044397 A1 * | 3/2004 | Stinson | 623/1.15 |
| 2004/0054354 A1 * | 3/2004 | Vito et al. | 606/1 |
| 2004/0225213 A1 * | 11/2004 | Wang et al. | 600/421 |

FOREIGN PATENT DOCUMENTS

EP 0 578 777 B1 1/1998

OTHER PUBLICATIONS

Jonathan Stinson, "Medical Devices and Methods of Making the Same", U.S. Appl. No. 10/229,548, filed Aug. 28, 2002.

Zhong et al., "Medical Devices with Magnetic Resonance Visibility Enhancing Material", U.S. Appl. No. 09/995,528, filed Nov. 27, 2001.

Dnyanesh Talpade, "Magnetic Resonance Imaging Devices with a Contrast Medium for Improved Imaging", U.S. Appl. No. 10/052,876, filed Oct. 19, 2001.

Zhong et al., "Coating a Medical Appliance with a Bubble Jet Printing Head", U.S. Appl. No. 09/895,415, filed Jul. 2, 2001.

Chin et al., "Multilayer Medical Device", U.S. Appl. No. 09/798,749, filed Mar. 2, 2001.

* cited by examiner

MRI-VISIBLE MEDICAL DEVICES

TECHNICAL FIELD

The invention relates to medical devices, including, for example, those are visible by magnetic resonance imaging.

BACKGROUND

Certain medical devices are inserted and/or implanted into the body of a patient. Examples of these devices include catheters, guidewires, medical balloons, stents, and stent-grafts. When a device is advanced through the body, its progress can be monitored, e.g., tracked, so that the device can be delivered properly to a target site. After the device is delivered to the target site, the device can be monitored to determine whether it has been placed properly and/or is functioning properly.

One method of monitoring a medical device is magnetic resonance imaging (MRI). MRI is a non-invasive technique that uses a magnetic field and radio waves to image the body. In some MRI procedures, the patient is exposed to a magnetic field, which interacts with certain atoms, e.g., hydrogen atoms, in the patient's body. Incident radio waves are then directed at the patient. The incident radio waves interact with atoms in the patient's body, and produce characteristic return radio waves. The return radio waves are detected by a scanner and processed by a computer to generate an image of the body.

In some MRI procedures, a contrast medium or agent is introduced into the body to enhance the visibility of an image. For example, the contrast agent can produce an area that is darker or lighter relative to other areas to enhance visibility. The contrast agent can alter the response of atoms near the contrast agent to the magnetic field. As a result, the interaction between the incident radio waves and the atoms can be altered, which consequently, can affect the return radio waves produced and the image generated.

SUMMARY

The invention relates to medical devices. In one aspect, the invention features a medical device having a member, e.g., a sealed, hollow, elongated member, and a contrast agent in the member. The contrast agent enhances the visibility of the device during MRI, X-ray fluoroscopy, and/or ultrasound imaging.

In another aspect, the invention features a medical device including a body, a sealed member in the body, the member being different than the body, and a contrast agent surrounded by or encapsulated by the member. The device is visible by magnetic resonance imaging.

A device is visible by magnetic resonance imaging when the device has a sufficient contrast to noise ratio under MRI. For example, a sufficient contrast to noise ratio may allow a user to define an edge of a device. In some embodiments, the device has a contrast to noise ratio greater than about 3, such as greater than 4, 5, 6, 7, 8 or higher.

Embodiments can include one or more of the following features. The contrast agent includes a liquid and/or a solid. The contrast agent includes a T1 relaxation time shortening agent. The contrast agent includes water and a chemical agent. The contrast agent includes a heavy metal complex, such as, for example, Gd-DTPA. The contrast agent includes glycerin. The contrast agent includes a T2 relaxation time shortening agent.

The member can have an aspect ratio greater than about one. The member can be a hollow fiber. The member can include a polymer material, such as, for example, polypropylene, polyethylene, Nylon, polyethyleneterephthalate (PET), or polyacetonitrile. The member can include a metal. The device can include a plurality of crisscrossing members in the body.

The device can further include a solid chemical agent encapsulated by the member. The solid chemical agent can be radiopaque. Examples of the solid chemical agent include materials having of gold, tantalum, barium, bismuth, or tungsten. The member can extend helically about the body.

The device can be a guidewire, a catheter, a vascular graft, a stent-graft, a stent, or a medical balloon, or a balloon catheter.

In another aspect, the invention features a method of making a medical device. The method can include extruding a body having a polymer and a member surrounding or encapsulating a contrast agent, wherein the device is visible by magnetic resonance imaging. The contrast agent can include a liquid and/or a solid.

In another aspect, the invention features a method of making a medical device including forming a mixture having a polymer and a member encapsulating a contrast agent, and forming the mixture into the medical device. The method can include injecting the mixture into a mold, and/or extruding the mixture. The contrast agent can include a liquid and/or a solid.

Embodiments can include one or more of the following advantages. The medical device has enhanced visibility, for example, during MRI, X-ray fluoroscopy, and/or ultrasound imaging. The contrast agent can be placed in a variety of devices.

The details of one or more embodiments are set forth in the accompanying drawings and the description below. Other aspects, features, and advantages of the invention will be apparent from the description, drawings, and claims.

DETAILED DESCRIPTION

Figure 1A:
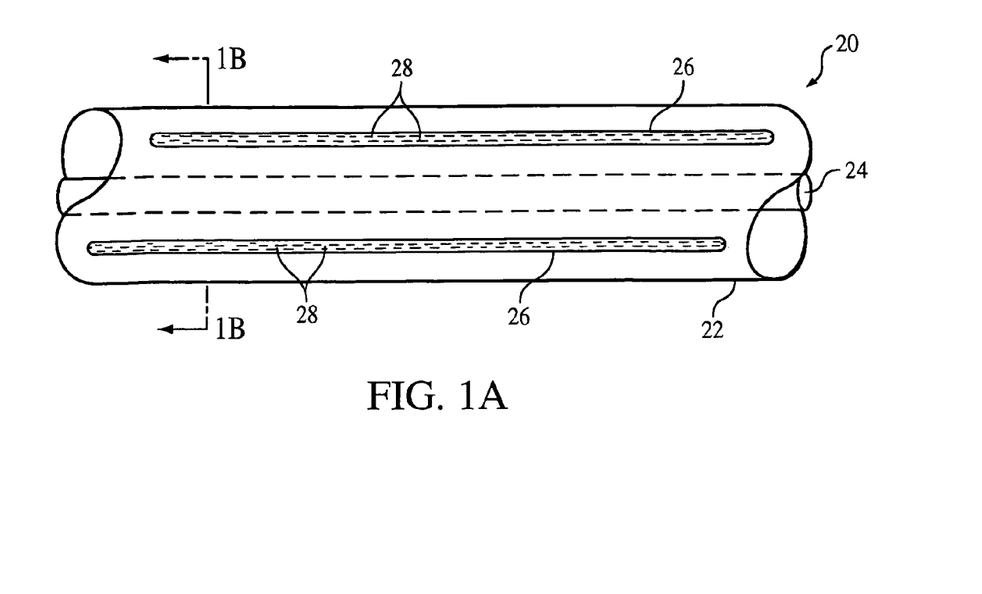
FIG. 1A is an illustration of a portion of an embodiment of a catheter.
Figure 1B:
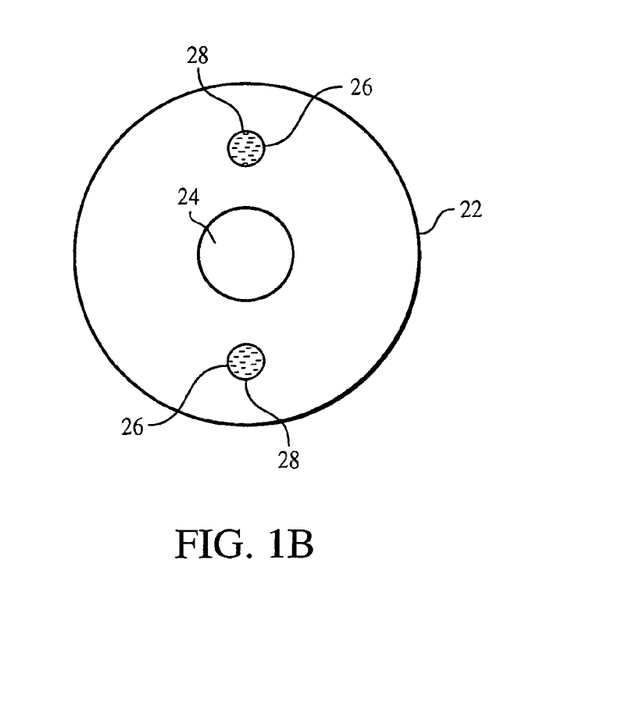
FIG. 1B is a cross-sectional view of the catheter of FIG. 1A, taken along line 1B-1B.

Referring to FIGS. 1A and 1B, a medical device 20, here, a portion of a catheter, includes a tubular body 22 defining a lumen 24, and a plurality of members 26 in the body. The catheter can be, e.g., a guiding catheter or a catheter shaft of a medical device such as a balloon catheter. Members 26 are sealed to encapsulate a contrast agent 28, and together, the members and the contrast agent can enhance the magnetic resonance imaging (MRI) visibility of catheter 20. As described below, members 26 and contrast agent 28 can be incorporated into other types of medical devices to enhance the MRI visibility of the devices.

Contrast agent 28 can be any material that enhances the MRI visibility of device 20. For example, contrast agent 28 can have an MRI response that is different than the MRI response of the medical device in which the contrast agent is used, and/or the MRI response of the bodily tissue or fluid near the contrast agent during use. The MRI response is the response to a magnetic field or radio waves used during MRI. In some embodiments, contrast agent 28 can include a material having a T1 relaxation time that is different than that of the medical device and/or tissue. For example, contrast agent 28 can include a liquid, such as a solution having a T1 (longitudinal) relaxation time shortening agent and a proton-containing fluid, such as water or glycerin. Examples of T1 relaxation time shortening agents include a paramagnetic metal salt or a paramagnetic metal chelate compound, such as heavy metal complexes, e.g., gadolinium diethylenetriaminepentaacetic acid (e.g., a 1% Gd-DTPA aqueous solution), GdDTPA-BMA, and GdHP-D03A (e.g., available from Schering, Nycomed and Bracco under the trade marks MAGNEVIST®, OMNISCAN®, and PROHANCE®). In some embodiments, the concentration of the T1 relaxation time shortening agent is about 1 μL of Gd-DTPA as supplied (e.g., 0.5 mole) per milliliter of saline to about 7 μL/mL, e.g., about 3 μL/mL. Alternatively or in addition, contrast agent 28 can include a material having a T2 relaxation time that is different than that of the medical device and/or tissue. For example, contrast agent 28 can include carrier or a fluid having ferromagnetic, ferrimagnetic, or superparamagnetic nanoparticles, such as iron oxide, dysprosium oxide, and/or gadolinium oxide. The particles can be surface modified, e.g., made hydrophilic, to suspend the particles in the fluid and reduce the occurrence of precipitation and/or coagulation. Examples of particles and methods of modifying the particles are described in U.S. Pat. Nos. 6,123,920 and 6,423,296, hereby incorporated by reference. In certain embodiments, a member 26 includes both T1 and a T2 relaxation time shortening agents. In some embodiments having multiple members 26, selected members include T1 relaxation time shortening agents, while different selected members include T2 relaxation time shortening agents.

Member 26 can be formed of one or more materials, such as non-magnetically active materials, that do not interfere with the MRI visibility of device 20. The material can be visibly transparent or opaque. Preferably, the material has a low permeability, e.g., impermeability, to fluids, such as water, in contrast agent 28. In some cases, the permeability is about equal to or less than the permeability of Nylon or PET. The low permeability to fluids reduces or prevents fluids from exiting member 26 and reducing the visibility of the contrast agent. Examples of suitable materials include polymers such as polypropylene, polyethylene, polysulfonate, Nylon, polyethyleneterephthalate (PET), or polyacetonitrile. Other materials include glass, and non-magnetic metals, such as aluminum. The material can be radiopaque, e.g., visible by X-ray fluoroscopy. Examples of radiopaque materials include those having a density greater than about 10 g/cc, gold, tantalum, tungsten, platinum, palladium, or their alloys. Different members 26 can be formed of different materials.

Member 26 is generally configured to house contrast agent 28. Member 26 can generally be a thin-walled receptacle defining a hollow cavity for housing contrast agent 26. The thin wall of member 26 allows more contrast agent 28 to be loaded into a given member 26, which can enhance visibility of the member, or reduce the overall size of the member.

Particular dimensions and/or configuration of member 26 can be function of, for example, the device in which the member is used, other components (such as guidewires) that can be used with the device, and/or the desired MRI visibility. Generally, member 28 can have a variety of configurations or shapes. Member 26 can be substantially spherical, oval, or elongated and relatively flexible. Member 26 can have a cross section that is circular or non-circular, such as oval, or regularly or irregularly polygonal having 3, 4, 5, 6, 7, or 8 or more sides. The outer surface of member 26 can be relatively smooth, e.g., cylindrical or rod-like, or faceted. Member 26 can have uniform or non-uniform thickness, e.g., the member can taper along its length. Different combinations of members 26 having two or more different configurations or shapes can be used in a medical device.

As noted above, the dimensions of member 26 can vary. In some cases, the width or outer diameter is between about 50 to about 500 microns. Member 26 can have a width or outer diameter greater than or equal to about 50 microns, 100 microns, 200 microns, 300 microns, or 400 microns; and/or less than or equal to about 500 microns, 400 microns, 300 microns, 200 microns, or 100 microns. The widths or outer diameters of multiple members 26 in a device can be uniform or relatively random. Member 26 can have a wall thickness between about 10 microns and about 500 microns. The wall thickness can be greater than or equal to about 10, 50, 100, 150, 200, 250, 300, 350, or 450 microns; and/or less than or equal to about 500, 450, 400, 350, 300, 250, 200, 150, 100, or 50 microns.

Different arrangements of members 26 are possible. An elongated member 26 can extend substantially an entire length of a medical device. Alternatively or in addition, members having similar or different dimensions can extend at selected portion(s) of the device. For example, members can act as marker, e.g., by placing the markers near the distal end of the device, or as a measuring tool, e.g., by placing the members at predetermined intervals. An elongated member can extend continuously or with gaps between members. Any number members can be included in a medical device, e.g., the device can have one or more elongated members, e.g., 2, 3, 4, 5, 6, 7, 8 or more. Member 26 can be equally and/or unequally spaced in a device. For example, looking at a radial cross section of a device having six members 26, the members can be formed at 2 o'clock, 3 o'clock, 4 o'clock, 8 o'clock, 9 o'clock, and 10 o'clock. Member 26 at 3 o'clock is equally spaced from the member at 2 o'clock and 4 o'clock; but, for example, the member at 4 o'clock is unequally spaced from member at 3 o'clock and 8 o'clock. Member 26 can be symmetrically or asymmetrically positioned in a medical device.

In some cases, members 26 are formed into relatively small fibers, e.g., chopped fibers, generally having lengths greater than widths or diameters. The fibers can have a length of about 0.5 mm to about 5 mm. In some embodiments, the fibers can have a length greater than or equal to about 0.5, 1.0, 1.5, 2.0, 2.5, 3.0, 3.5, 4.0, or 4.5 mm; and/or less than or equal to about 5.0, 4.5, 4.0, 3.5, 3.0, 2.5, 2.0, 1.5, or 1.0 mm. The lengths of the fibers can be uniform or relatively random. The fibers can be a width or outer diameter, and/or wall thickness generally as described above. The widths or outer diameters, and/or wall thickness can be uniform or relatively random.

In some embodiments, the fibers can be characterized as having a length to width aspect ratios from about 3:1 to about 20:1, although higher aspect ratios are possible. In some embodiments, the length to width aspect ratios can be greater than about 3:1, 5:1, 10:1, or 15:1; and/or less than about 20:1, 15:1, 10:1, or 5:1. The width used to determine the aspect ratio can be the narrowest or broadest width or outer diameter. The length can be the largest dimension of a fiber. Mixtures of fibers having two or more different aspect ratios can be used.

For a given medical device, the concentration of members 26 in fiber form is a function of, for example, the size of the fibers, the amount of contrast agent 28, the desired visibility, and/or the type of medical device. In some embodiments, the concentration is between about 10 and about 60 percent by weight. The concentration can be greater than or equal to about 10, 20, 30, 40, or 50 percent by weight; and/or less than or equal to about 60, 50, 40, 30, or 20 percent by weight.

Methods of forming member 26 can depend on the materials in the member. Generally, member 26 can be formed using conventional techniques, e.g., techniques used to form a hollow tube or filament, such as extrusion, drawing, or casting. Member 26 can be loaded with contrast agent 28 by injecting the contrast agent into the member or by soaking the member in the contrast agent. Member 26 can be sealed by heating (e.g., melting), gluing, and/or mechanically working (e.g., crimping) the member.

Similarly, methods of incorporating member 26 into a medical device can depend on the type of device. In some embodiments, a member, such as a relatively long polymer member, can be co-extruded with the device, such as a catheter, according to conventional techniques. In embodiments in which members 26 are in fiber form, the fibers can be mixed with a polymer of a device prior to extrusion or forming. The fibers can be randomly oriented or preferentially oriented. Methods of orienting a fiber are described in U.S. Ser. No. 10/229,548, filed on Aug. 28, 2002. Injection molding techniques can be used. For example, members 26 can be placed in a cavity of a mold, and material(s) of a device can be injected into the mold to form the device, such as a tube or a parison. In other embodiments, members 26 can be mixed with a device material and injected into the mold. Suitable device materials are described in U.S. Ser. No. 09/798,749, filed Mar. 2, 2001.

Figure 2:
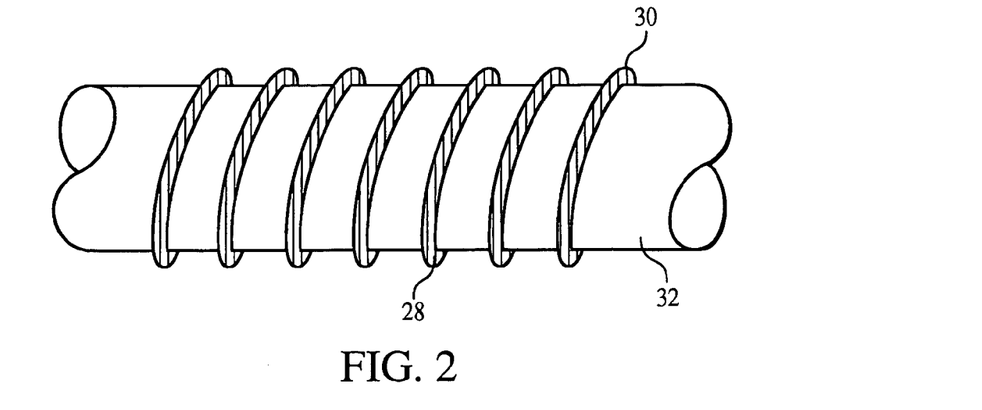
FIG. 2 is an illustration of a portion of an embodiment of a medical device.
Figure 3A:
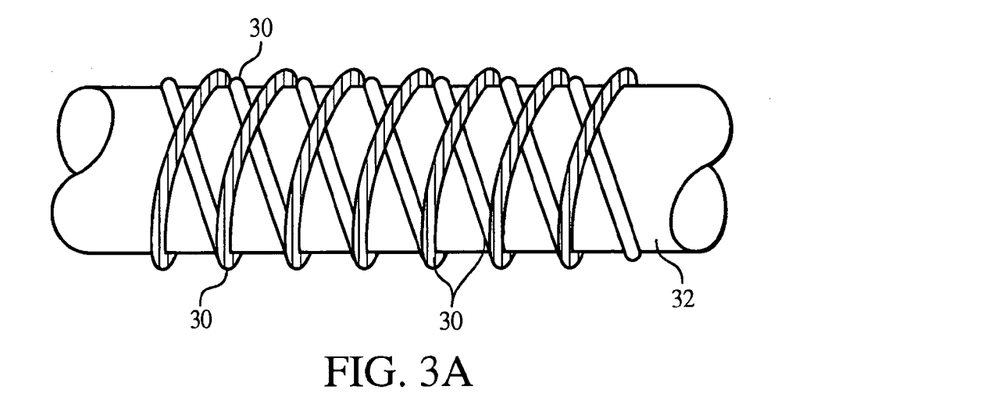
FIGS. 3A and 3B are illustrations of portions of embodiments of medical devices.
Figure 3B:
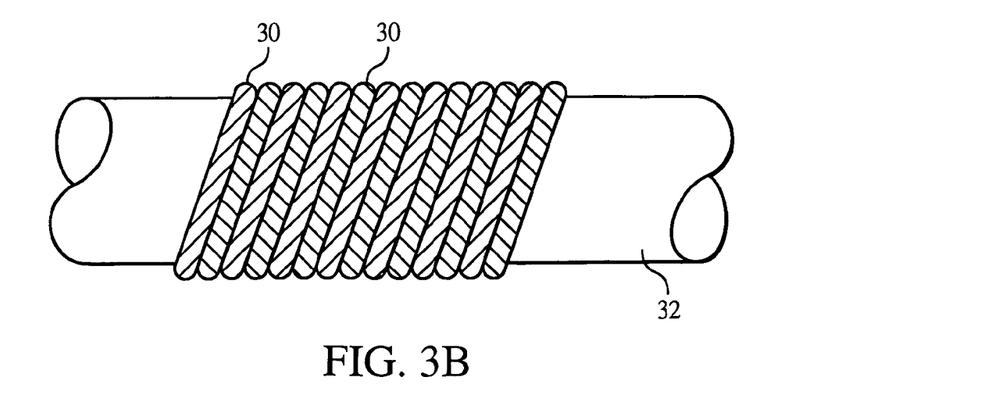

Other methods of incorporating member 26 into a medical device are possible. Referring to FIG. 2, an elongated and flexible member 30, e.g., made of a polymer, containing contrast agent 28 is helically wrapped around a portion of a medical device 32. Member 30 can be wrapped such that portions of the member contact each other around device 32 or wrapped such that the portions are spaced from each other (FIG. 2). Device 32 can be, for example, a guiding catheter, a guidewire, or a balloon catheter. Member 30 can be secured to device 32 by an adhesive and/or by selectively heating and melting the member to the device. In other embodiments, more than one elongated member 30 can be wrapped around device 32. Referring to FIG. 3A, multiple members 30 can be wrapped around device 32 in a woven, braided, or knitted pattern, which can enhance the strength of the device. In certain embodiments, multiple members 30 can be wrapped around device 32 without criss-crossing each other (FIG. 3B). The multiple members 30 can be the same or different. For example, selected members can have different contrast agents and/or be formed of different materials, as described above.

Figure 4:
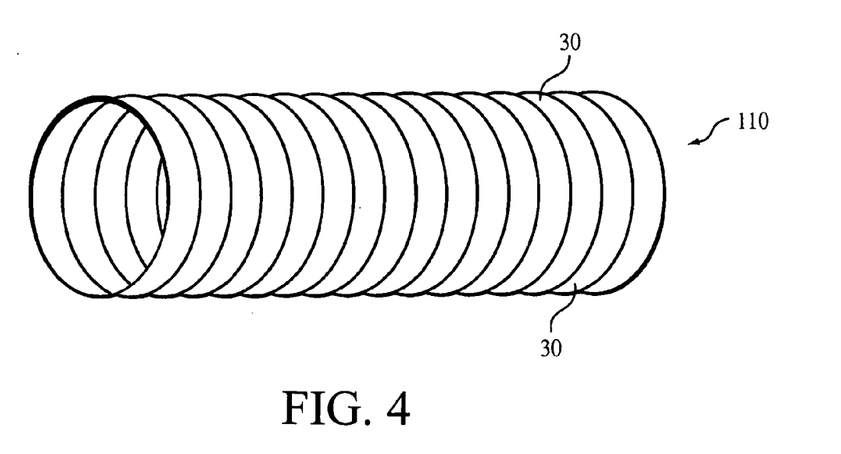
FIG. 4 is an illustration of a portion of an embodiment of a medical device.

In some embodiments, an elongated and flexible member, such as member 30, can be wound to form a medical device. Referring to FIG. 4, a medical device 110, such as a catheter, can be formed by winding an elongated member (e.g., member 30) around a mandrel, securing the member in place (e.g., by an adhesive), and removing the mandrel. The member defines a tube, which can be used, e.g., as a catheter or a vascular graft. The member can also be braided, knitted, or woven as described above to form a medical device (FIG. 3A or 3B).

After a medical device is incorporated with or formed by one or more members, the medical device can be used by conventional methods. The device can also be imaged by conventional imaging techniques.

Figure 5:
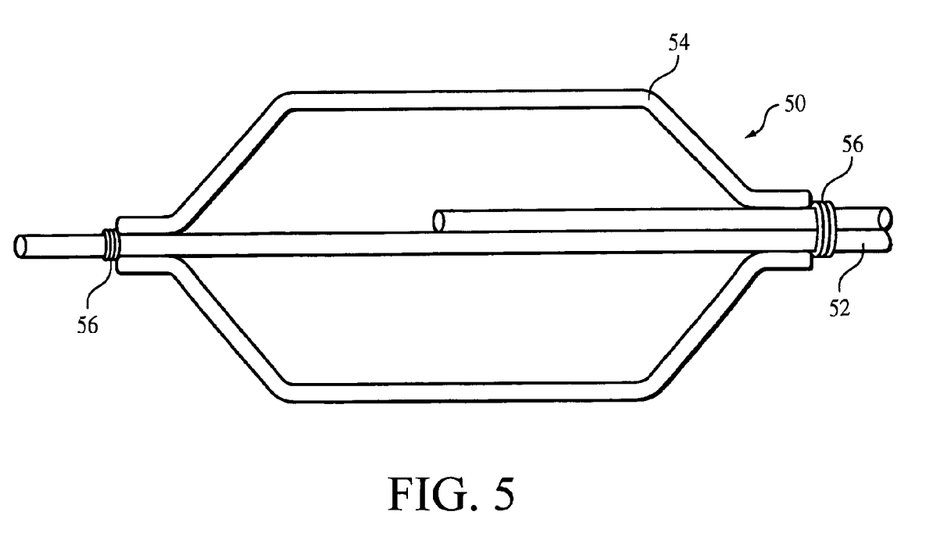
FIG. 5 is an illustration of a portion of an embodiment of a balloon catheter.

As noted above, member 26 or 30 and contrast agent 28 can be used in a variety of medical devices. Referring to FIG. 5, a balloon catheter 50 includes a catheter 52 and a medical balloon 54 carried by the catheter. In some embodiments, catheter 52 includes member 26 and/or 30 and contrast agent 28, as described above. Alternatively or in addition, medical balloon 54 can include member 26 and/or 30 and contrast agent 28 to enhance the balloon's MRI visibility. For example, fibers of member 26 can be compounded with a polymer and extruded to form a tube that can be formed into a balloon. Alternatively or in addition, balloon catheter 50 can include MRI visible markers 56 at selected portions, as shown, at the proximal and distal ends of balloon 54. Markers 56, for example, can indicate the location of balloon 54 when it is inflated to a recommended inflation volume. As shown, markers 56 are elongated members wound around selected portions of catheter 52. In other embodiments, members can be formed in catheter 52 at the selected portions, as described above. Examples of balloon catheters are described in, for example, Wang U.S. Pat. No. 5,195,969, and Hamlin U.S. Pat. No. 5,270,086, both hereby incorporated by reference; and are exemplified by the Ranger® system available from Boston Scientific Scimed, Maple Grove, Minn.

Figure 6:
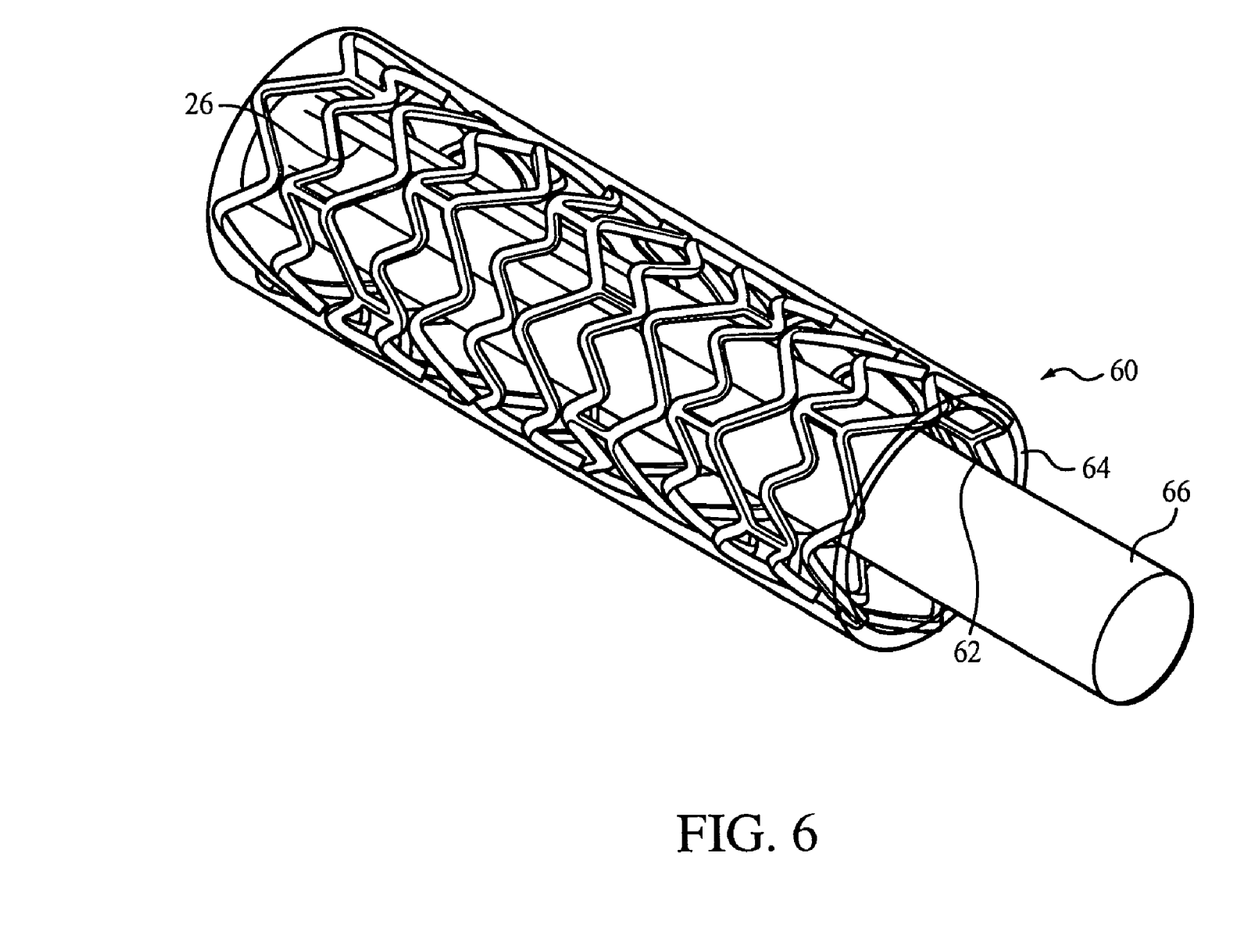
FIG. 6 is an illustration of a portion of an embodiment of a stent-graft.

Referring to FIG. 6, a stent-graft 60 includes a stent 62 and a graft 64 on the stent. Graft 64 includes member 26 and/or 30 and contrast agent 28, as described above. As shown, stent-graft 60 is carried by a support 66, which can be a catheter or a medical balloon, depending on the type of stent 62. Graft 64 can be formed of a biocompatible, non-porous or semi-porous polymer matrix made of polytetrafluoroethylene (PTFE), expanded PTFE, polyethylene, urethane, or polypropylene. Fibers of members 26 can be compounded with the polymer matrix. An elongated member 30 can extend, e.g., helically, around graft 63. Graft 64 can be defined by one or more members, e.g. FIG. 3A, 3B, or 4. In some embodiments, stent-graft 60 includes a releasable therapeutic agent or a pharmaceutically active compound, such as described in U.S. Pat. No. 5,674,242, entitled "Drug Delivery Particle", and filed on Aug. 30, 2002, and U.S. Ser. No. 09/895,415, filed Jul. 2, 2001, now U.S. Pat. No. 6,676,987, entitled "Coating a Medical Appliance With a Bubble Jet Printing Head". The therapeutic agents or pharmaceutically active compounds can include, for example, anti-thrombogenic agents, antioxidants, anti-inflammatory agents, anesthetic agents, anti-coagulants, and antibiotics.

In general, stent 62 can be of any desired shape and size (e.g., coronary stents, aortic stents, peripheral stents, gastrointestinal stents, urology stents and neurology stents). In certain embodiments, a coronary stent can have an expanded diameter of from about 2 millimeters to about 6 millimeters. In some embodiments, a peripheral stent can have an expanded diameter of from about 5 millimeters to about 24 millimeters. In certain embodiments, a gastrointestinal and/or urology stent can have an expanded diameter of from about 6 millimeters to about 30 millimeters. In some embodiments, a neurology stent can have an expanded diameter of from about 1 millimeter to about 12 millimeters. Stent 62 can be balloon-expandable, self-expandable, or a combination of both (e.g., as described in U.S. Pat. No. 5,366,504).

Stent-graft 60 can be used, e.g., delivered and expanded, according to conventional methods. Suitable catheter systems are described in, for example, Wang U.S. Pat. No. 5,195,969, and Hamlin U.S. Pat. No. 5,270,086. Suitable delivery methods are also exemplified by the NIR on Ranger® system, available from Boston Scientific Scimed, Maple Grove, Minn.

Figure 7:
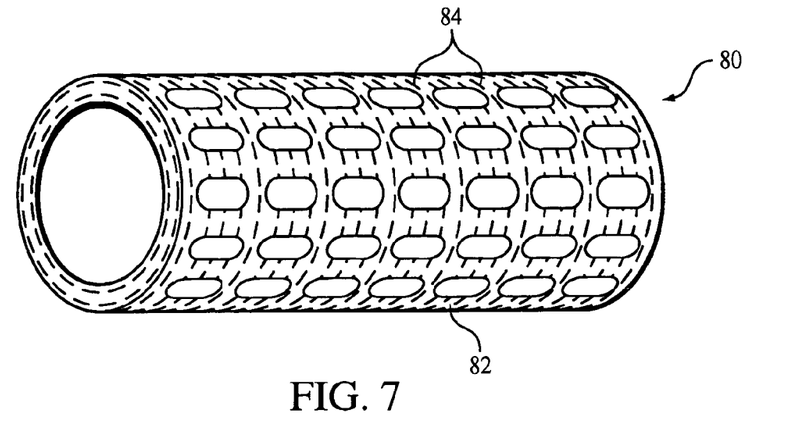
FIG. 7 is an illustration of a portion of an embodiment of a stent.

Referring to FIG. 7, member 26 or 30 can be incorporated into a stent 80. Stent 80 can be generally sized as described above for stent 62. Stent 80 includes a polymer matrix 82, and as shown, preferentially oriented fibers 84. Member 26 and/or 30 can be incorporated to matrix 82, as described above. Multiple embodiments of stent 80 including a polymer and methods of making the stents are described in U.S. Ser. No. 10/229,548, filed Aug. 28, 2002. In some embodiments, elongated members having a contrast agent can be used with conventional stent materials, e.g., stainless steel or Nitinol wires, to form a stent. For example, the elongated members can be co-knitted with the stent materials. Methods of forming the stent are described, for example, in Heath, U.S. Pat. No. 5,725,570, Mayer, U.S. Pat. No. 5,679,470, and Andersen, U.S. Pat. No. 5,366,504.

Figure 8:
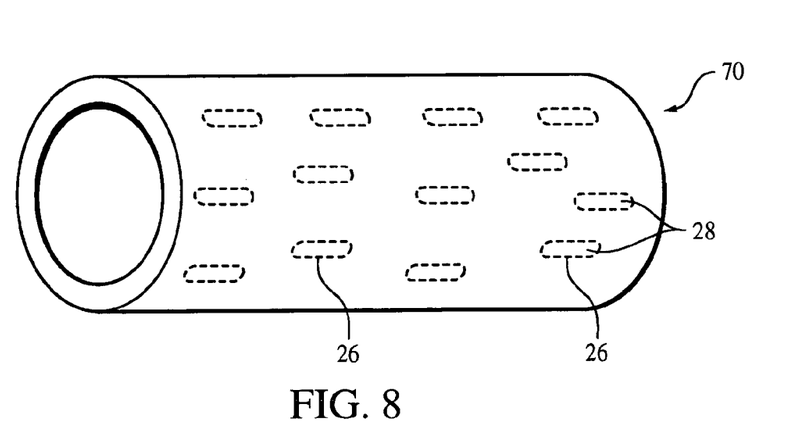
FIG. 8 is an illustration of a portion of an embodiment of a vascular graft.

Referring to FIG. 8, a vascular graft 70 includes a plurality of members 26 containing contrast agent 28. Member 26 and contrast agent 28 can be as generally described above, and can be arranged in the graft 70 as described above for catheter 20. For example, members 26 can be fibers compounded with a graft material and extruded to form graft. Alternatively or in addition, members 30 can be placed between multiple layers of graft material, with or without members 26 in the layers. Examples of graft materials, such as PTFE and expanded PTFE, and methods of making a graft are described in U.S. Pat. No. 6,428,571. Graft 70 can be formed by winding, braiding, weaving, or knitting elongated member(s), as described above (FIG. 2, 3A, or 3B).

Member 26 and/or 30 can be incorporated into a guidewire. Polymer guidewires and methods of making them are described in U.S. Pat. No. 6,436,056.

Member 26 and/or 30 can be incorporated into medical tubing, such as medical catheters. In general, the size and configuration of the tubing is not limited. In some embodiments, a catheter is in the form of a 10 French catheter or smaller, e.g., a 8 French, 6 French, 4 French, or 2 French catheter. A catheter can have a length of, for example, about 240 cm to about 3.5 meters. Examples of catheters include balloon catheters, aneurysm catheters, guide catheters, urology catheters, and microcatheters (all available from Boston Scientific Corp., Natick, Mass.).

In other embodiments, member 26 or 30 can contain a radiopaque material and/or an ultrasound contrast agent. Examples of radiopaque materials include tantalum, tungsten, platinum, palladium, or gold. The radiopaque material can be placed inside an member. Alternatively or in addition, the radiopaque material, e.g., a band of radiopaque material, can be placed on a medical device at selected positions, such as, for example, on a catheter adjacent to a balloon.

The ultrasound contrast agent can be any material that enhances visibility during ultrasound imaging. An ultrasound contrast agent can include a suspension having trapped bubbles of sufficient size to deflect sound waves. The ultrasound contrast agent can be incorporated into any embodiments of member 26 or 30 described above. Any of the medical devices described above can include members 26 or 30 having an MRI contrast agent, a radiopaque material, and/or an ultrasound contrast agent, in any combination or arrangement. For example, a device can include some members having an MRI contrast agent, and some members having an ultrasound contrast agent. A member can include more than one contrast agent, or one or more contrast agent with a radiopaque material.

Figure 9:
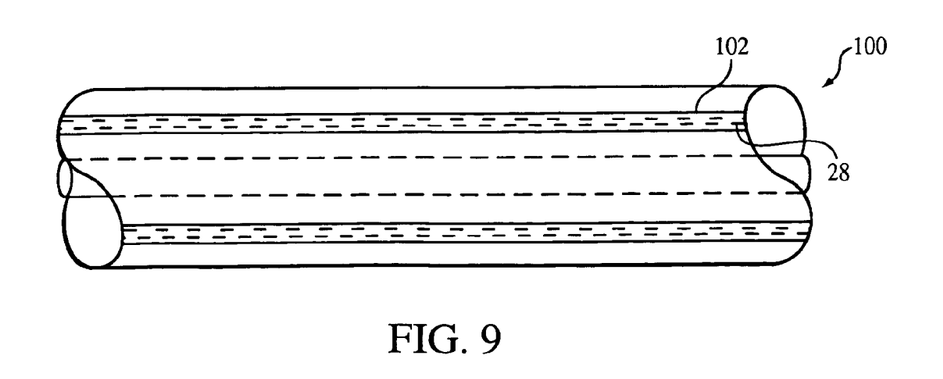
FIG. 9 is an illustration of a portion of an embodiment of a catheter.

In some embodiments, a member is not used to contain a contrast agent. For example, referring to FIG. 9, a catheter 100 can be formed to define a lumen 102, which is subsequently filled with a contrast agent, and sealed. Catheter 100 can additionally include members 26 or 30 with any contrast agent described above.

All patents, applications, references, and publications described herein are incorporated by reference in their entirety.

Other embodiments are within the scope of the following claims.

What is claimed is:

1. A medical device, comprising:
   a body formed of a polymer;
   a plurality of sealed members comprising a material different from the body, the members being embedded within the body, wherein the plurality of sealed members comprise relatively small fibers having a length-to-width aspect ratio of at least 3:1; and
   a contrast agent encapsulated within the sealed members, wherein the contrast agent is different than the sealed members;
   wherein the contrast agent is visible by magnetic resonance imaging,
   wherein the members are incorporated into the body by mixing the plurality of sealed members with the polymer to form a mixture prior to extrusion and extruding the mixture to form the body.

2. The device of claim 1, wherein the contrast agent has a contrast to noise ratio greater than about 4 under magnetic resonance imaging.

3. The device of claim 1, wherein the contrast agent comprises a liquid.

4. The device of claim 1, wherein the contrast agent comprises a solid.

5. The device of claim 1, wherein the contrast agent comprises a T1 relaxation time shortening agent.

6. The device of claim 1, wherein the contrast agent comprises water and a chemical agent.

7. The device of claim 1, wherein the contrast agent comprises a heavy metal complex.

8. The device of claim 7, wherein the heavy metal complex comprises Gd-DTPA.

9. The device of claim 1, wherein the contrast agent comprises glycerin.

10. The device of claim 1, wherein the contrast agent comprises a T2 relaxation time shortening agent.

11. The device of claim 1, wherein the members comprise a hollow fiber.

12. The device of claim 1, wherein the members comprise a polymer material.

13. The device of claim 12, wherein the polymer material is selected from a group consisting of polypropylene, polyethylene, Nylon, polyethyleneterephthalate, and polyacetonitrile.

14. The device of claim 1, wherein the members comprise a metal.

15. The device of claim 1, further comprising a solid chemical agent encapsulated by the members.

16. The device of claim 15, wherein the solid chemical agent is radiopaque.

17. The device of claim 16, wherein the solid chemical agent comprises a material selected from a group consisting of gold, tantalum, barium, bismuth, and tungsten.

18. The device of claim 1, wherein the members extend helically about the body.

19. The device of claim 1, wherein the device is a guidewire.

20. The device of claim 1, wherein the device is a vascular graft.

21. The device of claim 1, wherein the device is a stent-graft.

22. The device of claim 1, wherein the device is a stent.

23. The device of claim 1, wherein the device is a medical balloon.

24. The device of claim 1, wherein the device is a balloon catheter.

25. The device of claim 1, wherein the members comprise a material have low permeability.

26. A medical tubing, comprising:
a hollow body formed of a polymer;
a plurality of sealed members comprising a material different from the body, the sealed members being embedded within the body, wherein the plurality of sealed members comprise relatively small fibers having a length-to-width aspect ratio of at least 3:1; and
a contrast agent encapsulated within the sealed member, wherein the contrast agent is different than the sealed members;
wherein the contrast agent is visible by magnetic resonance imaging,
wherein the members are incorporated into the body by mixing the members with the polymer to form a mixture prior to extrusion and extruding the mixture to form the body.

27. The tubing of claim 26, in the form of a medical catheter.

28. A method of making a medical device, the method comprising:
extruding a body comprising a polymer, and a plurality of sealed members comprising a material different from the body and having a contrast agent encapsulated within the member, wherein the contrast agent is different than the sealed members, wherein the sealed members comprise relatively short fibers having a length-to-width aspect ratio of at least 3:1;
wherein the sealed members are embedded within the body and the device is visible by magnetic resonance imaging.

29. The method of claim 28, wherein the device has a contrast to noise ratio greater than about 4 under magnetic resonance imaging.

30. The method of claim 28, wherein the body is a tubular member.

31. The method of claim 28, wherein the contrast agent comprises a liquid.

32. The method of claim 28, wherein the contrast agent comprises a solid.

33. A method of making a medical device, the method comprising:
forming a mixture comprising a first polymer, and a plurality of sealed members comprising a material different from the first polymer and having a contrast agent that is different from the sealed members and encapsulated within the sealed members, wherein the sealed members are relatively short fibers having a length-to-width aspect ratio of at least 3:1; and
forming the mixture into the medical device;
wherein the members are embedded within the first polymer.

34. The method of claim 33, further comprising injecting the mixture into a mold.

35. The method of claim 33, further comprising extruding the mixture.

36. The method of claim 33, wherein the contrast agent comprises a liquid.

37. The method of claim 33, wherein the contrast agent comprises a solid.

* * * * *